US011660287B2

(12) United States Patent
Kobayashi et al.

(10) Patent No.: US 11,660,287 B2
(45) Date of Patent: May 30, 2023

(54) AGENT FOR PREVENTING OR TREATING SPINOCEREBELLAR ATAXIA

(71) Applicant: FUJIFILM Toyama Chemical Co., Ltd., Tokyo (JP)

(72) Inventors: Hiroshi Kobayashi, Tokyo (JP); Yoshihiko Matsumoto, Tokyo (JP); Tomohiro Okuda, Tokyo (JP)

(73) Assignee: FUJIFILM Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 16/617,660

(22) PCT Filed: Jun. 1, 2018

(86) PCT No.: PCT/JP2018/021224
§ 371 (c)(1),
(2) Date: Nov. 27, 2019

(87) PCT Pub. No.: WO2018/221730
PCT Pub. Date: Dec. 6, 2018

(65) Prior Publication Data
US 2020/0085787 A1 Mar. 19, 2020

(30) Foreign Application Priority Data

Jun. 2, 2017 (JP) .............................. JP2017-109885
Jun. 30, 2017 (JP) .............................. JP2017-128472
Jul. 27, 2017 (JP) .............................. JP2017-145101

(51) Int. Cl.
A61K 31/397 (2006.01)
A61P 25/28 (2006.01)

(52) U.S. Cl.
CPC ............ A61K 31/397 (2013.01); A61P 25/28 (2018.01)

(58) Field of Classification Search
None
See application file for complete search history.

(56) References Cited

U.S. PATENT DOCUMENTS

| 6,489,481 | B1 | 12/2002 | Keith et al. |
| 7,087,594 | B2 | 8/2006 | Saitoh et al. |
| 8,119,625 | B2 | 2/2012 | Iwakami et al. |
| 10,238,632 | B2 | 3/2019 | Yano |
| 11,541,033 | B2 | 1/2023 | Kobayashi et al. |
| 11,548,878 | B2 | 1/2023 | Yano et al. |
| 2005/0070521 | A1 | 3/2005 | Saitoh et al. |
| 2005/0250843 | A1 | 11/2005 | Nakada et al. |
| 2006/0194781 | A1 | 8/2006 | Saitoh et al. |
| 2006/0205709 | A1 | 9/2006 | Kimura et al. |
| 2009/0093453 | A1 | 4/2009 | Iwakami et al. |
| 2011/0224180 | A1 | 9/2011 | Pruss et al. |
| 2012/0028953 | A1 | 2/2012 | Roughley et al. |
| 2015/0045345 | A1 | 2/2015 | Inaba et al. |
| 2015/0166472 | A1 | 6/2015 | Kim et al. |
| 2015/0203472 | A1 | 7/2015 | Ceccarelli et al. |
| 2016/0324851 | A1 | 11/2016 | Friedhoff et al. |
| 2017/0129915 | A1 | 5/2017 | Tohda et al. |
| 2017/0165227 | A1 | 6/2017 | Takahashi et al. |
| 2018/0153855 | A1 | 6/2018 | Yano |
| 2018/0369194 | A1 | 12/2018 | Kano et al. |
| 2020/0108048 | A1 | 4/2020 | Kobayashi et al. |
| 2020/0155505 | A1 | 5/2020 | Kobayashi et al. |
| 2020/0215030 | A1 | 7/2020 | Kobayashi et al. |
| 2021/0137880 | A1 | 5/2021 | Kobayashi et al. |
| 2021/0198245 | A1 | 7/2021 | Yano et al. |

FOREIGN PATENT DOCUMENTS

| CN | 101432280 A | 5/2009 |
| CN | 104159583 A | 11/2014 |
| EP | 1 437 353 A1 | 7/2004 |
| EP | 3 100 725 A1 | 12/2016 |
| EP | 3 632 431 A1 | 4/2020 |
| JP | 2002-528489 A | 9/2002 |
| JP | 2011-513374 A | 4/2011 |
| KR | 10-2008-0111131 A | 12/2008 |
| RU | 2496784 C2 | 10/2013 |
| RU | 2015112914 A | 11/2016 |
| WO | 99/11293 A1 | 3/1999 |
| WO | 03/035647 A1 | 5/2003 |
| WO | 03/105830 A1 | 12/2003 |
| WO | 2007/125913 A1 | 11/2007 |
| WO | 2011/057199 A1 | 5/2011 |
| WO | 2013/125617 A1 | 8/2013 |

(Continued)

OTHER PUBLICATIONS

Sarva et al., Treatment Options in Degenerative Cerebellar Ataxia: A Systematic Review. Movement Disorders Clinical Practice, 2014, 1, 291-298.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Office Action dated Mar. 2, 2020 in corresponding Russian Application No. 2019138164.
Grimmer et al., "Beta Amyloid in Alzheimer's Disease: Increased Deposition in Brain Is Reflected in Reduced Concentration in Cerebrospinal Fluid", Biol. Psychiatry, 2009, vol. 65, No. 11, pp. 927-934 (17 pages total).

(Continued)

Primary Examiner — Po-Chih Chen
(74) Attorney, Agent, or Firm — Sughrue Mion, PLLC

(57) ABSTRACT

An object of the present invention is to provide an excellent drug for preventing or treating spinocerebellar ataxia. 1-(3-(2-(1-benzothiophen-5-yl)ethoxy)propyl)azetidin-3-ol or a salt thereof has an effect of suppressing brain atrophy, especially cerebellar atrophy, and is useful as an agent for preventing or treating spinocerebellar ataxia. Cerebellar atrophy observed in spinocerebellar ataxia can be prevented or treated by administering 1-(3-(2-(1-benzothiophen-5-yl)ethoxy)propyl)azetidin-3-ol or a salt thereof.

7 Claims, 1 Drawing Sheet

(56) References Cited

FOREIGN PATENT DOCUMENTS

| WO | 2015/115582 | A1 | 8/2015 |
|----|-------------|----|--------|
| WO | 2015/191506 | A2 | 12/2015 |
| WO | 2016/051799 | A1 | 4/2016 |
| WO | 2016/124508 | A1 | 8/2016 |
| WO | 2016/199878 | A1 | 12/2016 |
| WO | 2017/111005 | A1 | 6/2017 |

OTHER PUBLICATIONS

Kolobov et al., "Modern Pharmacological Models of Alzheimer's Disease", Original Articles, Experimental Neurology, 2014, vol. 8, No. 3, pp. 38-44 (32 pages total).
Office Action dated Oct. 23, 2020 in Russian Application No. 2019138538, corresponding to U.S. Appl. No. 16/617,607.
Office Action dated Sep. 25, 2020 in Russian Application No. 2019138166, corresponding to U.S. Appl. No. 16/617,739.
Tosun et al., "Relationship Between Regional Brain Amyloid-ß Deposition and Brain Atrophy Rates in Mild Cognitive Impairment", Alzheimer's & Dementia: The Journal of the Alzheimer's Association, Jul. 1, 2010, XP027440489, vol. 6, No. 4, p. e15 (total 1 page).
Extended European Search Report dated May 7, 2020 from European Patent Office in EP Application No. 18810520.9, corresponding to U.S. Appl. No. 16/617,739.
Schneider et al., "A Phase 2 Multicenter, Randomized, Placebo-Controlled Trial to Evaluate The Efficacy and Safety of Edonerpic (T-817) In Patients with Mild to Moderate Alzheimer's Disease", Alzheimer's & Dementia: The journal of the Alzheimer's Association, Jul. 19, 2017, P4-573. vol. 13, No. 7, XP085218926, p. P1572 (total 1 page).
Yamaguchi et al., "T-817MA, a neurotrophic compound, reverses Aß neurotoxicity and promotes neurite outgrowth through PI3-Kinase pathway in rat primary neurons", Abstract of the Annual Meeting of the Society for Neuroscience, Nov. 8, 2003, XP008135922, pp. 1-2 (total 2 pages).
Quinti et al., "A Novel Drug-Screening Platform in Microglial Cells Indentifies Potential AD Drugs", Alzheimer's & Dementia: The journal of the Alzheimer's Association, Jul. 19, 2017, XP085218817, P4-404, vol. 1, No. 13, p. P1485 (total 1 page).
Yano et al., "SIGMA-1 Receptor is a Molecular Target for Novel Neuropretectant T-817MA", Alzheimer's & Dementia: The Journal of the Alzheimer's Association, Jul. 1, 2015, XP029355158, P4-210, vol. 11, No. 7, p. P861 (total 1 page).
Nakagawa et al., "T-817MA, A Newly Developing Anti-Alzheimer's Agent, Protects Neurons And Recovers Memory Impairment in Amyloid B-Infused Rats and P301L Taumutated Mice", Alzheimer's & Dementia: The Journal of the Alzheimer's Association, Jul. 1, 2005, XP027823394, P-193, vol. 1, No. 1, p. S69-S70 (total 2 pages).
Extended European Search Report dated May 11, 2020 from European Patent Office in EP Application No. 18810759.3, corresponding to U.S. Appl. No. 16/617,584.
Extended European Search Report dated May 11, 2020 in European Application No. 18809579.8, corresponding to U.S. Appl. No. 16/617,552.
Extended European Search Report dated May 11, 2020 in European Application No. 18809739.8, corresponding to U.S. Appl. No. 16/617,660.
Extended European Search Report dated May 13, 2020 in European Application No. 18809110.2, corresponding to U.S. Appl. No. 16/617,607.
Office Action dated May 26, 2020 in Indian Application No. 201947049390, corresponding to U.S. Appl. No. 16/617,607.
Office Action dated May 26, 2020 in Indian Application No. 201947049392, corresponding to U.S. Appl. No. 16/617,660.
Office Action dated May 26, 2020 in Indian Application No. 201947049401, corresponding to U.S. Appl. No. 16/617,739.
Kawasaki et al., "A Neuroprotective Agent, T-817MA (1-{3-[2-(1-benzothiophen-5-yl)ethoxy]propyl}azetidin-3-ol Maleate), Prevents 1-methyl-4-phenyl-1,2,3,6-tetrahydropyridine-induced Neurotoxicity in Mice", Neuropharmacology, vol. 55, Issue 5, Oct. 2008, pp. 654-660, Abstract only.
Office Action dated Aug. 10, 2020 in Australian Application No. 2018276638, subject matter—related to U.S. Appl. No. 16/617,552.
Office Action dated Aug. 14, 2020 in Australian Application No. 2018277981, subject matter—related to U.S. Appl. No. 16/617,552.
Office Action dated Aug. 17, 2020 in Australian Application No. 2018277983, subject matter—related to U.S. Appl. No. 16/617,552.
Office Action dated Aug. 21, 2020 in Australian Application No. 2018277982, subject matter—related to U.S. Appl. No. 16/617,552.
Office Action dated Jul. 3, 2020 in Russian Application No. 2019138699, corresponding to U.S. Appl. No. 16/617,552.
Office Action dated Apr. 27, 2020 from Russian Patent Office in Russian Application No. 2019138166/04, corresponding to U.S. Appl. No. 16/617,739.
International Search Report dated Jul. 24, 2018 in International Application No. PCT/JP2018/021225, corresponding to U.S. Appl. No. 16/617,552.
Written Opinion dated Jul. 24, 2018 in International Application No. PCT/JP2018/021225, corresponding to U.S. Appl. No. 16/617,552.
International Search Report dated Sep. 4, 2018 in International Application No. PCT/JP2018/021222, corresponding to U.S. Appl. No. 16/617,584.
Written Opinion dated Sep. 4, 2018 in International Application No. PCT/JP2018/021222, corresponding to U.S. Appl. No. 16/617,584.
International Search Report dated Jul. 24, 2018 in corresponding International Application No. PCT/JP2018/021223, corresponding to U.S. Appl. No. 16/617,739.
Written Opinion dated Jul. 24, 2018 in corresponding International Application No. PCT/JP2018/021223, corresponding to U.S. Appl. No. 16/617,739.
International Search Report dated Jul. 24, 2018 in International Application No. PCT/JP2018/021224.
Written Opinion dated Jul. 24, 2018 in International Application No. PCT/JP2018/021224, corresponding to U.S. Appl. No. 16/617,660.
International Search Report dated Jul. 24, 2018 in International Application No. PCT/JP2018/021226, corresponding to U.S. Appl. No. 16/617,607.
Written Opinion dated Jul. 24, 2018 in International Application No. PCT/JP2018/021226, corresponding to U.S. Appl. No. 16/617,607.
International Preliminary Report on Patentablity dated Dec. 3, 2019 in International Application No. PCT/JP2018/021222, corresponding to U.S. Appl. No. 16/617,584.
International Preliminary Report on Patentablity dated Dec. 3, 2019 in corresponding International Application No. PCT/JP2018/021223.
International Preliminary Report on Patentablity dated Dec. 3, 2019 in International Application No. PCT/JP2018/021224, corresponding to U.S. Appl. No. 16/617,660.
International Preliminary Report on Patentablity dated Dec. 3, 2019 in International Application No. PCT/JP2018/021225, corresponding to U.S. Appl. No. 16/617,552.
International Preliminary Report on Patentablity dated Dec. 3, 2019 in International Application No. PCT/JP2018/021226, corresponding to U.S. Appl. No. 16/617,607.
"2012 Alzheimer's Disease Facts and Figures", Alzheimer's Association, 2012 (72 pages total); http://www.alz.org/downloads/facts_figures_2012.pdf.
Sugimoto, "Development of Anti-Alzheimer's Disease Drug Based on Beta-Amyloid Hypothesis", Yakugaku Zasshi, 2010, vol. 130, No. 4, pp. 521-526 (6 pages total).
"Epidemiological studies on Alzheimer's disease in Japan", Japanese Journal of Clinical Medicine, 2008, vol. 66 (Extra ed. 1), pp. 23-27 (5 pages total).
Press Release by Seed Planning (Dec. 28, 2010) (3 pages total); http://www.seedplanning.co.jp/press/2010/2010122801.html.
Japanese Journal of Clinical Psychopharmacology, 2011, vol. 14, No. 7, pp. 1123-1129.
Japanese Journal of Clinical Psychopharmacology, 2012, vol. 15, No. 3, pp. 311-321.

(56) References Cited

OTHER PUBLICATIONS

Takamura et al., "Effects of the neurotrophic agent T-817MA on oligomeric amyloid-β-induced deficits in long-term potentiation in the hippocampal CA1 subfield", Neurobiology of Aging, 2014, vol. 35, pp. 532-536 (5 pages total).
Fujifilm Corp., "II stage clinical experiment in the United States for Alzheimer's dementia therapeutic drug 'T-817MA': drastically restricting, with statistical significant difference, progress of deterioration in cognitive function with respect to patient group having this innovative two effects of reducing phosphorylation tau in cerebrospinal fluid and restricting hippocampal atrophy in brain", News release, Jul. 19, 2017 (1 page total).
Mckhann et al., "The diagnosis of dementia due to Alzheimer's disease: Recommendations from the National Institute on Aging—Alzheimer's Association workgroups on diagnostic guidelines for Alzheimer's disease", Alzheimer's Dement., May 2011, vol. 7, No. 3, pp. 263-269, (52 pages total).
Kimura et al., "T-817MA, a neurotrophic agent, ameliorates the deficits in adult neurogenesis and spatial memory in rats infused i.c.v. with amyloid-β peptide", British Journal of Pharmacology, 2009, vol. 157, pp. 451-463 (13 pages total).
Moreno et al., "Blocking effects of human tau on squid giant synapse transmission and its prevention by T-817MA", Frontiers in Synaptic Neuroscience, May 2011, vol. 3, Article 3, pp. 1-8 (8 pages total).
Fukushima et al., "T-817MA, a neuroprotective agent, attenuates the motor and cognitive impairments associated with neuronal degeneration in P301L tau transgenic mice", Biochemical and Biophysical Research Communications, 2011, vol. 407, pp. 730-734 (5 pages total).
Fukushima, "Pharmacological properties of T-817MA, a novel neurotrophic agent, for treatment of Alzheimer's disease", Folia Pharmacologica Japonica, 2010, vol. 136, pp. 11-14 (2 pages total).
Proceedings of the Annual Meeting of the Japanese Research Group on Senile Dementia, 2010, vol. 15, pp. 79-81 (4 pages total).
Lo et al., "Longitudinal Change of Biomarkers in Cognitive Decline", Archives of Neurology, 2011, vol. 68, No. 10, pp. 1257-1266 (10 pages total).
Japanese Journal of Geriatrics, 2013, vol. 50, No. 1, pp. 1-8 (9 pages total).
Jack Jr. et al., "Tracking pathophysiological processes in Alzheimer's disease: an updated hypothetical model of dynamic biomarkers", Lancet Neurology, Feb. 2013, vol. 12, No. 2, pp. 207-216 (10 pages total).
Hirata et al., "A Novel Neurotrophic Agent, T-817MA [1-{3-[2-(1-Benzothiopen-5-yl) Ethoxy] Propyl}-3-azetidinol Maleate], Attenuates Amyloid-β-Induced Neurotoxicity and Promotes Neurite Outgrowth in Rat Cultured Central Nervous System Neurons", The Journal of Pharmacology and Experimental Therapeutics, vol. 314, No. 1, pp. 252-259, 2005 (8 pages total).
Office Action dated May 29, 2020 in Russian Application No. 2019138538, corresponding to U.S. Appl. No. 16/617,607.
Uehara et al., "T-817MA, a novel neurotrophic agent, ameliorates loss of GABAergic parvalbumin-positive neurons and sensorimotor gating deficits in rats transiently exposed to MK-801 in the neonatal period", Journal of Psychiatric Research, vol. 46, No. 5, pp. 622-629, 2012 (8 pages total).
Office Action dated May 26, 2020 in Indian Application No. 201947049400.
Office Action dated Dec. 8, 2020, issued by the Korean Intellectual Property Office in Korean Application No. 10-2019-7035347, corresponding to U.S. Appl. No. 16/617,739.
Office Action dated Dec. 8, 2020, issued by the Korean Intellectual Property Office in Korean Application No. 10-2019-7035348, corresponding to U.S. Appl. No. 16/617,660 (the present application).
Office Action dated Dec. 9, 2020, issued by the Korean Intellectual Property Office in Korean Application No. 10-2019-7035350, corresponding to U.S. Appl. No. 16/617,607.
Office Action dated Dec. 9, 2020, issued by the Korean Intellectual Property Office in Korean Application No. 10-2019-7035349, corresponding to U.S. Appl. No. 16/617,552.
Hearing Notice dated Jan. 8, 2021, issued by the Indian Intellectual Property Office in Indian Application No. 201947049401, corresponding to U.S. Appl. No. 16/617,739.
U.S. Appl. No. 16/617,584, Hiroshi Kobayashi, et al., filed Nov. 27, 2019, Pending.
U.S. Appl. No. 16/617,739, Hiroshi Kobayashi, et al., filed Nov. 27, 2019, Pending.
U.S. Appl. No. 16/617,660 (the present application), Pending.
U.S. Appl. No. 16/617,552, Hiroshi Kobayashi, et al., filed Nov. 27, 2019, Pending.
U.S. Appl. No. 16/617,607, Hiroshi Kobayashi, et al., filed Nov. 27, 2019, Pending.
Office Action dated Jan. 27, 2021 issued by the Canadian Patent Office in Application No. 3,067,453, corresponding to U.S. Appl. No. 16/617,739.
Office Action dated Jan. 27, 2021 issued by the Canadian Patent Office in Application No. 3,067,455, corresponding to U.S. Appl. No. 16/617,660.
Hearing Notice dated Jan. 8, 2021 issued by the Indian Patent Office in application No. 201947049392, corresponding to U.S. Appl. No. 16/617,660.
Office Action dated Jan. 27, 2021 issued by the Canadian Patent Office in Application No. 3,067,456, corresponding to U.S. Appl. No. 16/617,552.
Hearing Notice dated Feb. 3, 2021 issued by the Indian Patent Office in Application No. 201947049400, corresponding to U.S. Appl. No. 16/617,552.
Office Action dated Jan. 29, 2021 issued by the Canadian Patent Office in Application No. 3,067,458, corresponding to U.S. Appl. No. 16/617,607.
Hearing Notice dated Feb. 3, 2021 issued by the Indian Patent Office in Application No. 201947049390, corresponding to U.S. Appl. No. 16/617,607.
Decision under section 15 dated Feb. 23, 2021, issued in Indian Application No. 201947049401, corresponding to U.S. Appl. No. 16/617,739.
Office Action dated Feb. 17, 2021, issued in Russian Application No. 2019138166/04, corresponding to U.S. Appl. No. 16/617,739.
Blennow, "Cerebrospinal Fluid Protein Biomarkers for Alzheimer's Disease", The American Society for Experimental NeuroTherapeutics, Apr. 2004, vol. 1, pp. 213-225 (13 pages total).
Office Action dated Jun. 25, 2021 in Korean Application No. 10-2019-7035347, corresponding to U.S. Appl. No. 16/617,739.
Office Action dated Jul. 2, 2021 in U.S. Appl. No. 16/617,552.
Office Action dated Jun. 10, 2021 in Russian Application No. 2019138538, corresponding to U.S. Appl. No. 16/617,607.
Grigorenko et al., "Molecular Basics of Alzheimer's Disease", Molekulyarnaya Biologiya, 2007, vol. 41, No. 2, pp. 331-345 (15 pages total).
Lemere et al., "Sequence of Deposition of Heterogeneous Amyloid β-Peptides and APO E in Down Syndrome: Implications for Initial Events in Amyloid Plaque Formation", Neurobiology of Disease, 1996, vol. 3, No. 1, pp. 16-32, Article No. 0003 (17 pages total).
Office Action dated Jun. 10, 2021 in Mexican Application No. MX/a/2019/014306, corresponding to U.S. Appl. No. 16/617,607.
Office Action dated Jun. 24, 2021 in Korean Application No. 10-2019-7035349, corresponding to U.S. Appl. No. 16/617,552.
Office Action dated Jun. 24, 2021 in Korean Application No. 10-2019-7035350, corresponding to U.S. Appl. No. 16/617,607.
Office Action dated Jul. 13, 2021 in Japanese Application No. 2019-521350, corresponding to U.S. Appl. No. 16/617,552.
Shimohama et al., Journal of Japan Senile Medicine, vol. 50, No. 1, pp. 50:1-50:8, 2013 (8 pages total).
Office Action dated Jun. 25, 2021 in Korean Application No. 10-2019-7035348, corresponding to U.S. Appl. No. 16/617,660 (the present application).
Manto et al., "Animal Models of Human Cerebellar Ataxias: a Cornerstone for the Therapies of the Twenty-First Century", Cerebellum, 2009, vol. 8, pp. 137-154 (18 pages total).

(56) References Cited

OTHER PUBLICATIONS

Office Action dated Jul. 21, 2021 in New Zealand Application No. 759647.
Decision under section 15 dated Mar. 22, 2021 issued in Indian patent application No. 201947049392.
Office Action dated Jun. 1, 2021 issued in Singapore patent application No. 11201911515Q.
Mascalchi et al., "Progression of Brain Atrophy in Spinocerebellar Ataxia Type 2: A Longitudinal Tensor-Based Morphometry Study", PLOS One, 2014, vol. 9, Issue 2, pp. 1-7, e89410.
Office Action dated Aug. 19, 2021 in U.S. Appl. No. 16/617,584.
Shigemori et al., "The factorial structure of the mini mental state examination (MMSE) in Japanese dementia patients", BMC Geriatrics, 2010, vol. 10, Issue 36, pp. 1-7.
Colovic et al., "Acetylcholinesterase inhibitors: Pharmacology and Toxicology", Current Neuropharmacology, 2013, vol. 11, pp. 315-335.
Office Action dated Jun. 23, 2021 in U.S. Appl. No. 16/617,739.
Jagust, "Is amyloid-ß harmful to the brain? Insights from human imaging studies", Brain, 2016, vol. 139, pp. 23-30.
Healthline, "Brain Atrophy (Cerebral Atrophy)", updated Mar. 29, 2019 https://www.healthline.com/health/brain-atrophy (10 pages total).
Office Action dated Jun. 23, 2021 in U.S. Appl. No. 16/617,607.
Nguyen et al., "Ameliorative Effects of a Neuroprotective Agent, T-817MA, on Place Learning Deficits Induced by Continuous Infusion of Amyloid-ß Peptide (1-40) in Rats", Hippocampus, 2007, vol. 17, pp. 443-455.
Office Action dated Jul. 22, 2021 in New Zealand Application No. 759662, corresponds to U.S. Appl. No. 16/617,607.
Office Action dated Jul. 21, 2021 in New Zealand Application No. 759657, corresponds to U.S. Appl. No. 16/617,552.
Office Action dated Jul. 21, 2021 in New Zealand Application No. 759585, corresponds to U.S. Appl. No. 16/617,739.
Decision under section 15 dated Mar. 22, 2021 issued in Indian patent application No. 201947049390, corresponds to U.S. Appl. No. 16/617,607.
Office Action dated Jun. 1, 2021 issued in Singapore patent application No. 11201911512S, corresponds to U.S. Appl. No. 16/617,739.
Office Action dated Jun. 1, 2021 issued in Singapore patent application No. 11201911519U, corresponds to U.S. Appl. No. 16/617,607.
Office Action dated Jun. 1, 2021 issued in Singapore patent application No. 11201911520U, corresponds to U.S. Appl. No. 16/617,552.
Tosun et al., "Spatial patterns of brain amyloid-β burden and atrophy rate associations in mild cognitive impairment", Brain, 2011, vol. 134, pp. 1077-1088.
Communication dated Aug. 11, 2021 from the Canadian Patent Office in Canadian Application No. 3,067,458, corresponds to U.S. Appl. No. 16/617,607.
Communication dated Aug. 17, 2021 from the Mexican Patent Office in Mexican Application No. MX/a/2019/014306, corresponds to U.S. Appl. No. 16/617,607.
Communication dated Aug. 4, 2021 from the Canadian Patent Office in Canadian Application No. 3,067,456, corresponds to U.S. Appl. No. 16/617,552.
Notice of Final Rejection dated Aug. 24, 2021 from the Korean Patent Office in Korean Application No. 10-2019-7035348.
Office Action dated Nov. 9, 2021 in U.S. Appl. No. 16/617,607.
Restriction Requirement dated Jun. 3, 2021 in U.S. Appl. No. 16/760,512.
Office Action dated Aug. 18, 2021 in U.S. Appl. No. 16/760,512.
Marquer et al., "Increasing membrane cholesterol of neurons in culture recapitulates Alzheimer's disease early phenotypes", Molecular Neurodegeneration, 2014, vol. 9, No. 60, pp. 1-13 (13 pages total).
Chemical Abstracts Registry No. 519187-30-5, Indexed in the Registry file on STN CAS Online, May 23, 2003 (1 page total).
Bae et al., "Cholesterol biosynthesis from Ianosterol: molecular cloning, chromosomal localization, functional expression and liver-specific gene regulation of rat sterol $\Delta^8$-isomerase, a cholesterogenic enzyme with multiple functions", Biochem. J., 2001, vol. 353, pp. 689-699 (11 pages total).
Berardi et al., "Novel 4-(4-Aryl)cyclohexyl-1-(2-pyridyl)piperazines as $\Delta_8$-$\Delta_7$ Sterol Isomerase (Emopamil Bonding Protein) Selective Ligands with Antiproliferative Activity", J. Med. Chem., 2008, vol. 51, No. 23, pp. 7523-7531 (9 pages total).
Communication dated Jul. 3, 2020, from the European Patent Office in application No. 1887344.5, corresponds to U.S. Appl. No. 16/760,512.
Derry et al., "Mutations in a $\Delta^8$-$\Delta^7$ sterol isomerase in the tattered mouse and X-linked dominant chondrodysplasia punctata", Nature Genetics, Jul. 1999, vol. 22, pp. 286-290 (5 pages total).
International Preliminary Report on Patentability dated May 5, 2020, issued by the International Bureau in application No. PCT/JP2018/040283, corresponds to U.S. Appl. No. 16/760,512.
International Search Report dated Jan. 29, 2019, issued by the International Searching Authority in application No. PCT/JP2018/040283, corresponds to U.S. Appl. No. 16/760,512.
Laggner et al., "Discovery of High-Affinity Ligands of $\sigma_1$ Receptor, ERG2, and Emopamil Binding Protein by Pharmacophore Modeling and Virtual Screening", J. Med. Chem., 2005, vol. 48, No. 15, pp. 4754-4764 (11 pages total).
Moebius et al., "Identification of a 27-kDa High Affinity Phenylalkylamine-Binding Polypeptide as the $\sigma_1$ Binding Site by Photoaffinity Labeling and Ligand-Directed Antibodies", Molecular Pharmacology, 1993, vol. 44, pp. 966-971 (8 pages total).
Silve et al., "Emopamil-binding Protein, a Mammalian Protein That Binds a Series of Structurally Diverse Neuroprotective Agents, Exhibits $\Delta 8$-$\Delta 7$ Sterol Isomerase Activity in Yeast", The Journal of Biological Chemistry, Sep. 13, 1996, vol. 271, No. 37, pp. 22434-22440 (8 pages total).
Written Opinion dated Jan. 29, 2019, issued by the International Searching Authority in application No. PCT/JP2018/040283, corresponds to U.S. Appl. No. 16/760,512.
Office Action dated Nov. 4, 2021 in Mexican Application No. MX/a/2019/014306, corresponds to U.S. Appl. No. 16/617,607.
Decision of Refusal dated Nov. 30, 2021 from the Japanese Patent Office in Japanese Application No. 2019-521350, corresponds to U.S. Appl. No. 16/617,552.
"Guidance for Industry: Estimating the Maximum Safe Starting Dose in Initial Clinical Trials for Therapeutics in Adult Healthy Volunteers", U.S. Department of Health and Human Services, Food and Drug Administration, Center for Drug Evaluation and Research (CDER), Pharma and Toxicology, 2005, pp. 1-27 (30 pages total).
Final Office Action dated Dec. 8, 2021 in U.S. Appl. No. 16/760,512.
Office Action dated Dec. 9, 2021 in Mexican Application No. MX/a/2019/014300, corresponding to U.S. Appl. No. 16/617,552.
Office Action dated Dec. 15, 2021 in U.S. Appl. No. 16/617,739.
Busciglio et al., "Altered Metabolism of the Amyloid β Precursor Protein Is Associated with Mitochondrial Dysfunction in Down's Syndrome", Neuron, 2002, vol. 33, pp. 677-688 (12 pages total).
Chetelat et al., "Relationship between Atrophy and β-Amyloid Deposition in Alzheimer Disease", Ann Neurol, 2010, vol. 67, pp. 317-324 (8 pages total).
Office Action dated Dec. 14, 2021 in Korean Application No. 10-2019-7035349, corresponds to U.S. Appl. No. 16/617,552.
Office Action dated Dec. 14, 2021 in Korean Application No. 10-2019-7035350, corresponds to U.S. Appl. No. 16/617,607.
Office Action dated Dec. 20, 2021 in Korean Application No. 10-2019-7035347, corresponds to U.S. Appl. No. 16/617,739.
Office Action dated Jan. 28, 2022 in U.S. Appl. No. 16/617,552.
Office Action dated Feb. 14, 2022 in U.S. Appl. No. 16/617,607.
Office Action dated Jan. 25, 2022 in Russian Application No. 2019138538, corresponds to U.S. Appl. No. 16/617,607.
Head et al., "Alzheimer's Disease in Down Syndrome", Eur J Neurodegener Dis., 2012, vol. 1, No. 3, pp. 353-364 (16 pages total).
Aisen et al., "On the path to 2025: understanding the Alzheimer's disease continuum", Alzheimer's Research & Therapy, 2017, vol. 9, No. 60, pp. 1-10 (10 pages total).

(56) References Cited

OTHER PUBLICATIONS

A. Sugiyama and H. Shimada, "Tau PET Imaging for Dementia in Clinical Practice", Radioisotopes, vol. 65, No. 12, pp. 517-522 (Japan Radioisotope Association, 2016) (6 pages total).
Naoji Amano, "Neurodegenerative Diseases and Tauopathy", Shinshu Journal, 2002, vol. 50, No. 3, pp. 113-120 (8 pages total).
Y. Soeda and A. Takashima, "Development of disease modifying drugs for dementia—focusing on anti-tau drugs", Clinical Neurology, vol. 54, pp. 1178-1180 (2014) (3 pages total).
Y. Yoshiyama, Nippon Rinsho, Japanese Journal of Clinical Medicine, vol. 69, Suppl. 8, pp. 262-266 (2011) (5 pages total).
H. Takahashi, "Animal models of Alzheimer's disease for preclinical research", Folia Pharmacol. Jpn., vol. 136, No. 1, pp. 6-10 (2010) (5 pages total).
Office Action dated Feb. 18, 2022 for Canadian Application No. 3,067,456; 4 pages.
Notice of Allowance dated Mar. 14, 2022 in U.S. Appl. No. 16/617,584.
Office Action dated Mar. 2, 2022 issued in corresponding Mexican patent application No. MX/a/2019/014302, 8 pages.
Office Action dated Mar. 3, 2022 issued in the related Mexican patent application No. MX/a/2019/014310, 10 pages.
Notice of Allowance dated Apr. 1, 2022 in U.S. Appl. No. 16/617,739.
Office Action dated Mar. 1, 2022 in Mexican Application No. MX/a/2019/014306, corresponds to U.S. Appl. No. 16/617,607.
Notice of Allowance dated Apr. 4, 2022 in U.S. Appl. No. 16/617,607.
Office Action dated Apr. 4, 2022 in New Zealand Application No. 759662, corresponds to U.S. Appl. No. 16/617,607.
Office Action dated Mar. 31, 2022 in Korean Application No. 10-2019-703530, corresponds to U.S. Appl. No. 16/617,607.
Communication dated Apr. 12, 2022 from the Korean Patent Office in Korean Application No. 10-2019-7035347, corresponds to U.S. Appl. No. 17/617,739.
Communication dated Apr. 7, 2022 from the Korean Patent Office in Korean Application No. 10-2019-7035349, corresponds to U.S. Appl. No. 16/617,552.
Office Action dated May 6, 2022 in corresponding Chinese Application 201880035501.X.
Office Action dated May 24, 2022 in corresponding Japanese Application No. 2019-521349.
Peng Ying et al., "Progress of clinical trials in Alzheimer's disease drugs", Acta Pharmaceutica Sinica, 2016, vol. 51, No. 8, pp. 1185-1195 (11 pages total).
Office Action dated May 6, 2022 in Chinese Application No. 201880035394.0, corresponds to U.S. Appl. No. 16/617,739.
Office Action dated May 6, 2022 in Chinese Application No. 201880035503.9, corresponds to U.S. Appl. No. 16/617,552.
Office Action dated May 6, 2022 in Chinese Application No. 201880035521.7, corresponds to U.S. Appl. No. 16/617,607.
Office Action dated May 10, 2022 in Japanese Application No. 2019-521348, corresponds to U.S. Appl. No. 16/617,739.
Office Action dated May 10, 2022 in Japanese Application No. 2019-521347, corresponds to U.S. Appl. No. 16/617,584.
Reconsideration Report by Examiner dated Apr. 28, 2022 in Japanese Application No. 2019-521350, corresponds to U.S. Appl. No. 16/617,652.
Buccarello et al., "Sex Impact on Tau-Aggregation and Postsynaptic Protein Levels in the P301L Mouse Model of Tauopathy" Journal of Alzheimer's Disease, 2017, vol. 56, No. 4, pp. 1279-1292 (27 pages total).
Office Action dated Jun. 6, 2022 in U.S. Appl. No. 16/617,552.
Zheng et al., "Amyloid β Peptide induces Tau Phosphorylation and Loss of Cholinergic Neurons in Rat Primary Septal Cultures", Neuroscience, 2022, vol. 115, No. 1, pp. 201-211 (11 pages total).
Office Action dated Jun. 7, 2022 in Japanese Application No. 2019-521351, corresponds to U.S. Appl. No. 16/617,607.
Office Action dated Apr. 12, 2022 in Israeli Application No. 270910.
Office Action dated Jul. 26, 2022 in Brazilian Application No. BR1120190249834, corresponds to U.S. Appl. No. 16/617,607.
Allowance dated Aug. 15, 2022 in U.S. Appl. No. 16/617,584.
Office Action dated Aug. 15, 2022 in U.S. Appl. No. 16/617,739.
Office Action dated Aug. 16, 2022 in U.S. Appl. No. 16/617,607.
Office Action dated Jun. 26, 2022 in Israeli Application No. 270912, corresponds to U.S. Appl. No. 16/617,552.
Office Action dated Jun. 27, 2022 in israeli Application No. 270922, corresponds to U.S. Appl. No. 16/617,739.
Office Action dated Aug. 29, 2022 in Korean Application No. 10-2022-7022765, corresponds to U.S. Appl. No. 16/617,552.
Office Action dated Aug. 29, 2022 in Korean Application No. 10-2022-7022766, corresponds to U.S. Appl. No. 16/617,552.
Office Action issued in Brazilian Application No. BR112019024851-0 dated Sep. 13, 2022, corresponds to U.S. Appl. No. 16/617,739.
Office Action issued in Brazilian Application No. BR1120190248811 dated Sep. 13, 2022.
Office Action dated Oct. 18, 2022 by Japan Patent Office in Japanese Application No. 2019-550404, which corresponds to U.S. Appl. No. 16/760,512.
Office Action dated Nov. 8, 2022 in Japanese Application No. 2019-521351, corresponds to U.S. Appl. No. 16/617,607.
Office Action dated Nov. 15, 2022 in Japanese Application No. 2019-521347, corresponds to U.S. Appl. No. 16/617,584.
Office Action dated Nov. 15, 2022 in Japanese Application No. 2019-521348, to corresponds to U.S. Appl. No. 16/617,739.
Herman Moreno, et al., "Blocking effects of human tau on squid giant synapse transmission and its prevention by T-817 MA", Frontiers in Synaptic Neuroscience, 2011, vol. 2, Article 3, 8 pages.
Mario Mascalchi, et al., "Progression of Brian Atrophy in Spinocerebellar Ataxia Type 2: A Longitudinal Tensor-Based Morphometry Study", PLOS One, Feb. 2014, vol. 9, Issue 2, e89410, 7 pages.
Official Action dated Jan. 5, 2023 issued in the corresponding Singapore patent application 11201911515Q.
Tatsuo Kimura, et al., "T-817MA, a neurotrophic agent ameilorates the deficits in adult neurogenesis and spatial memory in rats infused i.c.v. with amyloid-β peptide", British Journal of Pharmacology, 2009, vol. 157, pp. 451-463.
Tetsuo Fukushima, "New regulation neurotrophic factor-like low molecular weight compound T817MA", 2019, 2 pages.
Tetsuo Fukushima, et al., "T-817MA, a neuroprotective agent, attenuates the motor and cognitive impairments associated with neuronal degeneration in P301L tau transgenic mice", Biochemical and Biophysical Research Communications, 2011, vol. 407, pp. 730-734.
Yusaku Takamura, et al., "Effects of the neurotrophic agent T-817MA on oligomeric amyloid-β-induced deficits in long-term potentiation in the hippocampal CA1 subfield", Nuerobiology of Aging, 2014, vol. 35, pp. 532-536.
Decision of Refusal dated Jan. 18, 2023 issued in the related Chinese patent application No. 201880035394.0, corresponds to U.S. Appl. No. 16/617,739.
Duygu Tosun, et al., "Spatial patterns of brain amloid-β burden and atrophy rate associations in mild cognitive impairment", Brain A Journal of Neurology, 2011, vol. 134, pp. 1077-1088.
Masaya Nakagawa, et al., "T-817MA, A Newly Developing Anti-Alzheimer's Agent, Protects Neurons and Recovers Memory Impairment in Amloid B-Infused Rats and P301L TAU-Mutated Mice", Abstracts: Pharmacological Treatments, 1 (Suppl 1), 2005, pp. S69-S70.
Ni-Chung Lee, et al, "Blood Beta-Amyloid and Tau in Down Syndrome: A Comparison with Alzheimer's Disease", Frontiers in Aging Neuroscience, Jan. 17, 2017, vol. 8, Aritcle 316 (8 pages).
Official Action dated Jan. 18, 2023 issued in the related Chinese patent application No. 201880035503.9, corresponds to U.S. Appl. No. 16/617,552.
Official Action dated Jan. 18, 2023 issued in the related Chinese patent application No. 201880035521.7, corresponds to U.S. Appl. No. 16/617,607.
Official Action dated Jan. 5, 2023 issued in the related Singapore patent application No. 11201911512S, corresponds to U.S. Appl. No. 16/617,739.
Official Action dated Jan. 5, 2023 issued in the related Singapore patent application No. 11201911519U, corresponds to U.S. Appl. No. 16/617,607.

(56) References Cited

OTHER PUBLICATIONS

Official Action dated Jan. 5, 2023 issued int he related Singapore patent application No. 11201911520U, corresponds to U.S. Appl. No. 16/617,552.

Preeti J. Khandelwal, et al., "Wild type and P301L mutatn Tau promote neuro-inflammation and α-Synuclein accumulation in lenitviral gene delivery modles", Mol Cell Neurosci, Jan. 2012, vol. 49, No. 1; pp. 44-53.

W.-H. Zheng, et al., "Amyloid β Peptide Induces Tau Phosphorylation and Loss of Cholinergic Neurons in Rat Primary Septal Cultures", Neuroscience, 2002, vol. 115, No. 1, pp. 201-211.

Notice of Allowance dated Dec. 7, 2022 in U.S. Appl. No. 16/617,739.

Notice of Allowance dated Dec. 7, 2022 in U.S. Appl. No. 16/617,607.

Office Action dated Jan. 10, 2023 in U.S. Appl. No. 16/617,552.

Ramesh J. L. Kandimalla, et al., "CSF p-Tau levels in the prediction of Alzheimer's disease", Biology Open 2, 2013, pp. 1119-1124.

Official Action dated Mar. 7, 2023 issued in Japanese patent application No. 2022-028810, corresponding to U.S. Appl. No. 16/617,552.

Official Action dated Mar. 7, 2023 issued in Japanese patent application No. 2022-028811, corresponding to U.S. Appl. No. 16/617,552.

Office Action dated Mar. 27, 2023, in Korean Patent Application No. 10-2022-7022765, corresponding to U.S. Appl. No. 16/617,552 (Eng. translation only).

Office Action dated Mar. 27, 2023, in Korean Patent Application No. 10-2022-7022766, corresponding to U.S. Appl. No. 16/617,552 (Eng. translation only).

"History of Changes for Study: NCT02079909: Efficacy and Safety of T-817MA in Patients with Mild to Moderate Alzheimer's Disease (US202)", ClinicalTrials.gov.archive, U.S. National Library of Medicine, May 16, 2017 (13 pages).

\* cited by examiner

[Figure 1]
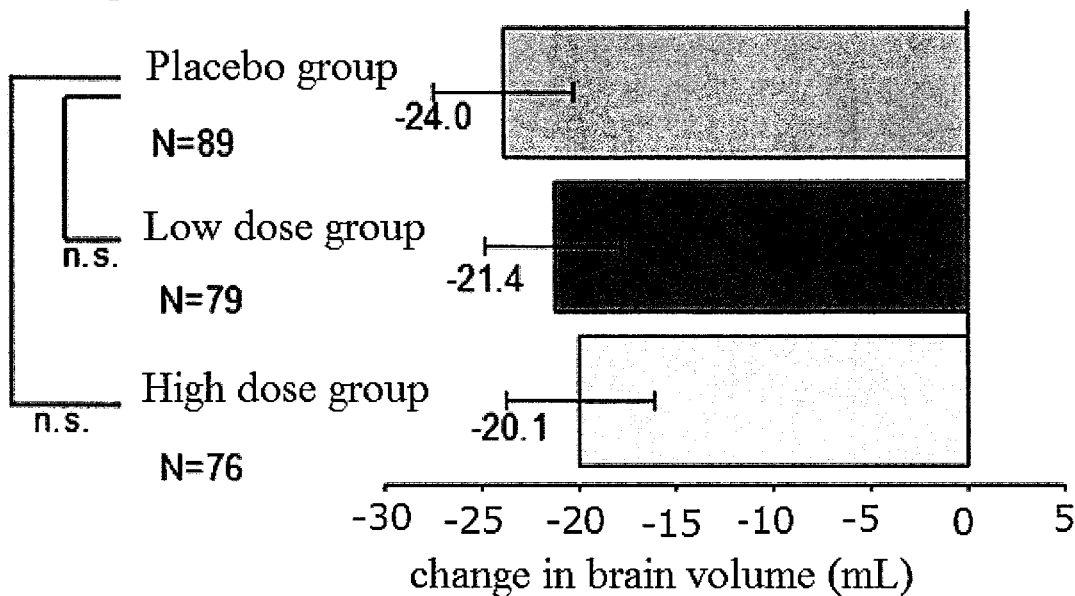
[Figure 2]
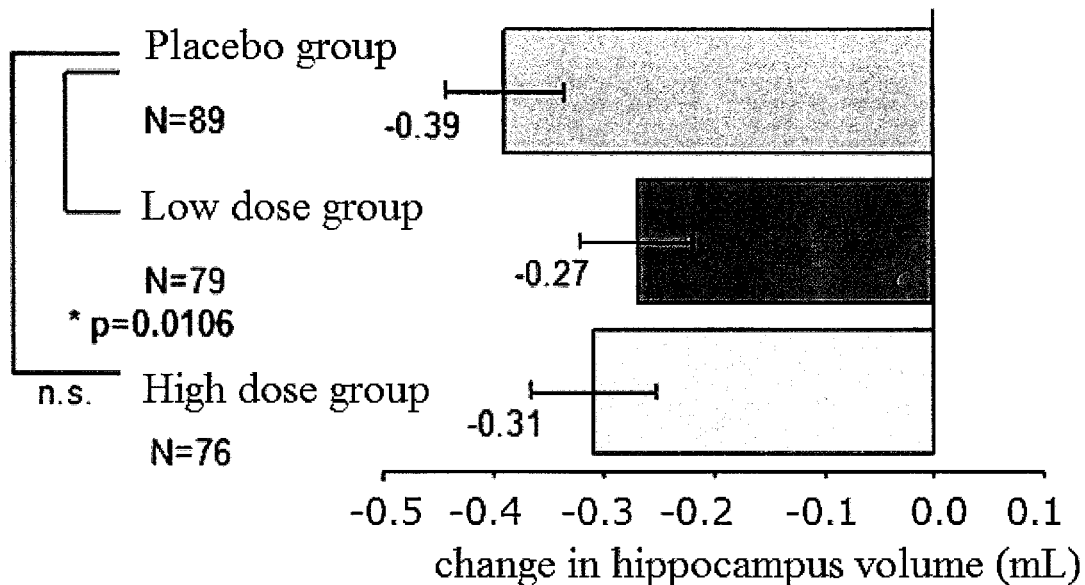

AGENT FOR PREVENTING OR TREATING SPINOCEREBELLAR ATAXIA

CROSS REFERENCE TO RELATED APPLICATIONS

This application is a National Stage of International Application No. PCT/JP2018/021224 filed Jun. 1, 2018, claiming priority based on Japanese Patent Application No. 2017-109885 filed Jun. 2, 2017; Japanese Patent Application No. 2017-128472 filed Jun. 30, 2017; and Japanese Patent Application No. 2017-145101 filed Jul. 27, 2017.

TECHNICAL FIELD

The present invention relates to an agent for preventing or treating spinocerebellar ataxia, comprising 1-(3-(2-(1-benzothiophen-5-yl)ethoxy)propyl)azetidin-3-ol or a salt thereof as an active ingredient.

BACKGROUND ART

Spinocerebellar ataxia is a neurodegenerative disease whose main symptoms are cerebellar or posterior column ataxia and spastic paraplegia. Spinocerebellar ataxia can be roughly divided into two types: hereditary spinocerebellar ataxia and non-hereditary spinocerebellar ataxia. Examples of hereditary spinocerebellar ataxia include hereditary olivopontocerebellar atrophy, hereditary cortical cerebellar atrophy, spinocerebellar ataxia type 1, spinocerebellar ataxia type 2, spinocerebellar ataxia type 3 (Machado-Joseph disease), spinocerebellar ataxia type 6, spinocerebellar ataxia type 31, hereditary dentatorubropallidoluysian atrophy, ataxia telangiectasia, Friedreich's ataxia, ataxia with vitamin E deficiency, aprataxin deficiency, senataxin deficiency, spastic ataxia of Charlevoix-Saguenay and hereditary spastic paraplegia. Examples of non-hereditary spinocerebellar ataxia include olivopontocerebellar atrophy, Shy-Drager syndrome, striatonigral degeneration and cortical cerebellar atrophy. While spinocerebellar ataxia with an initial symptom of cerebellar ataxia has been called olivopontocerebellar atrophy, one with an initial symptom of parkinsonism has been called striatonigral degeneration, and one with significant autonomic neuropathy such as orthostatic hypotension has been called Shy-Drager syndrome, from the fact that in all cases symptoms overlap as the disease progresses, brainstem and cerebellar atrophy and striatal abnormalities are found and there are common histopathological findings, these diseases may be collectively called multiple system atrophy.

For drug therapy, thyrotropin-releasing hormone (TRH) or TRH derivatives are used for all ataxia symptoms. Drugs symptomatically used for each disease include mexiletine hydrochloride for painful muscle cramps and acetazolamide for episodic dystonia and symptoms of dizziness.

1-(3-(2-(1-benzothiophen-5-yl)ethoxy)propyl)azetidin-3-ol (hereinafter referred to as "Compound A") or a salt thereof is known to have neuroprotective, nerve regeneration-promoting and neurite outgrowth actions, and be useful as a therapeutic agent for central and peripheral neurological diseases (Patent Literature 1). Furthermore, a publication discloses that usually the drug may be administered to an adult in a dose or divided doses of 0.01 to 500 mg per day (Patent Literature 2).

PRIOR ART LITERATURES

Patent Literature

Patent Literature 1: International Publication No. WO 2003/035647
Patent Literature 2: International Publication No. WO 2003/105830

SUMMARY OF INVENTION

Problem to be Solved by the Invention

An object of the present invention is to provide an excellent drug for preventing or treating spinocerebellar ataxia.

Means for Solving Problem

In such circumstances, the present inventors have found that Compound A or a salt thereof has an effect of suppressing cerebellar atrophy and have completed the present invention.

The present invention provides the following.

(1) An agent for preventing or treating spinocerebellar ataxia, comprising Compound A or a salt thereof as an active ingredient.

(2) The agent for preventing or treating spinocerebellar ataxia according to (1), wherein the spinocerebellar ataxia is hereditary olivopontocerebellar atrophy, hereditary cortical cerebellar atrophy, spinocerebellar ataxia type 3 (Machado-Joseph disease), spinocerebellar ataxia type 6, spinocerebellar ataxia type 31 or cortical cerebellar atrophy.

(3) The agent for preventing or treating spinocerebellar ataxia according to (1) or (2), wherein the agent is for suppressing cerebellar atrophy in a patient with spinocerebellar ataxia.

(4) The agent for preventing or treating spinocerebellar ataxia according to (1) or (2), wherein the agent is for improving ataxia in a patient with spinocerebellar ataxia.

(5) The agent for preventing or treating spinocerebellar ataxia according to (1) or (2), wherein the agent is for improving balance disorder in a patient with spinocerebellar ataxia.

(6) The agent for preventing or treating spinocerebellar ataxia according to any one of (1) to (5), wherein the agent is orally administered in a dose of 100 mg to 400 mg in terms of Compound A once a day.

(7) The agent for preventing or treating spinocerebellar ataxia according to any one of (1) to (5), wherein the agent is orally administered in a dose of 160 mg or 320 mg in terms of Compound A once a day.

The present invention also provides the following.

(a) A pharmaceutical composition for preventing or treating spinocerebellar ataxia, comprising Compound A or a salt thereof as an active ingredient.

(b) Compound A or a salt thereof for use in prevention or treatment of spinocerebellar ataxia.

(c) A method of preventing or treating spinocerebellar ataxia, comprising administering Compound A or a salt thereof to a patient.

(d) Use of Compound A or a salt thereof for producing an agent for preventing or treating spinocerebellar ataxia.

(e) An agent for suppressing cerebellar atrophy, comprising Compound A or a salt thereof as an active ingredient.

(f) Compound A or a salt thereof for use in suppression of cerebellar atrophy.

(g) A method of suppressing cerebellar atrophy, comprising administering Compound A or a salt thereof to a patient.

(h) Use of Compound A or a salt thereof for producing an agent for suppressing cerebellar atrophy.

Advantageous Effects of Invention

Brain atrophy, in particular cerebellar atrophy, can be suppressed and spinocerebellar ataxia can be prevented or treated by administering Compound A or a salt thereof.

BRIEF DESCRIPTION OF DRAWINGS

FIG. 1 is a graph showing change in brain volume (the whole brain) at week 52 from that at screening in Test Example 1. "n.s." means that there was no statistically significant difference.

FIG. 2 is a graph showing change in brain volume (the hippocampus) at week 52 from that at screening in Test Example 1. "n.s." means that there was no statistically significant difference.

EMBODIMENTS FOR CARRYING OUT THE INVENTION

Hereinafter the present invention will be described in detail.

In the present description, the respective terms have the following meaning unless otherwise specified.

In the present description, the numerical range shown with "to" represents a range inclusive of the value before and after "to" as the minimum and maximum value, respectively.

Compound A means 1-(3-(2-(1-benzothiophen-5-yl)ethoxy)propyl)azetidin-3-ol.

Examples of salts of Compound A include known salts of a basic group such as amino group or an acidic group such as hydroxyl group or carboxyl group.

Examples of salts of a basic group include salts with a mineral acid such as hydrochloric acid, hydrogen bromide, nitric acid and sulfuric acid; salts with an organic carboxylic acid such as formic acid, acetic acid, citric acid, oxalic acid, fumaric acid, maleic acid, succinic acid, malic acid, tartaric acid, aspartic acid, trichloroacetic acid and trifluoroacetic acid; and salts with a sulfonic acid such as methanesulfonic acid, benzenesulfonic acid, p-toluenesulfonic acid, mesitylenesulfonic acid and naphthalenesulfonic acid.

Examples of salts of an acidic group include salts with an alkali metal such as sodium and potassium; salts with an alkaline earth metal such as calcium and magnesium; ammonium salts; and salts with a nitrogen-containing organic base such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-efenamin and N,N'-dibenzylethylenediamine.

Of the above salts, pharmacologically acceptable salts are preferred, and salts with maleic acid are more preferred.

In the case where Compound A or a salt thereof has isomers (e.g., optical isomers, geometric isomers and tautomers), the present invention includes all these isomers and also includes hydrates, solvates and any crystal forms thereof.

Prevention means to prevent the onset of a specific disease or at least one symptom caused by the disease.

Treatment means to reduce or improve at least one symptom caused by a specific disease with which a subject is affected, and delay the progress of the disease.

In an embodiment of the present invention, prevention means to inhibit or delay the onset or progress of spinocerebellar ataxia. Treatment means to inhibit or delay the progress of spinocerebellar ataxia.

In another embodiment of the present invention, prevention means to inhibit or delay the onset or progress of cerebellar atrophy. Treatment means to inhibit or delay the progress of cerebellar atrophy.

Mild to moderate Alzheimer's disease may be clinically diagnosed as "probable AD" according to the diagnosis criteria provided by the National Institute of Neurological and Communicative Disorders and Stroke/the Alzheimer's Disease and Related Disorders Associations (NINCDS-ADRDA).

A usual doctor may reasonably make clinical diagnosis of "mild to moderate Alzheimer's disease" using standard criteria. For example, according to the score of the standardized Mini-Mental State Examination (MMSE, scores of 0 to 30), clinical diagnosis of mild to moderate, moderate, or moderate to severe AD is provided. The MMSE (Folstein, Folstein and McHugh, 1975) is a simple test of cognitive function including an interview with patients. Orientation, memory, calculation and attention, language skills and other functions are assessed. The total score is 30. The lower the score, the higher the level of impairment of cognitive function.

In Test Examples of the present invention, patients with an MMSE score of 12 to 22 at the start of the test (screening) were determined as mild to moderate AD. Note that the MMSE is not the only way to clinically determine the grade of AD, though convenient.

Apolipoprotein E (ApoE), one of the apolipoproteins, constitutes lipoprotein and is involved in recognition of lipoprotein and lipid metabolism. ApoE has 3 isoforms of ApoE2, ApoE3 and ApoE4. A report shows that ApoE4 genotype encoding ApoE4 is correlated with the amount of deposition of amyloid-β protein in the brain and the ApoE4 genotype is a risk gene of Alzheimer's disease.

Structural change in the brain is observed is also observed in normal aging, while cerebellar atrophy is a structural abnormality peculiar to spinocerebellar ataxia, which causes, for example, ataxia.

In an embodiment of the present invention, spinocerebellar ataxia includes, for example, hereditary olivopontocerebellar atrophy, hereditary cortical cerebellar atrophy, spinocerebellar ataxia type 1, spinocerebellar ataxia type 2, spinocerebellar ataxia type 3 (Machado-Joseph disease), spinocerebellar ataxia type 6, spinocerebellar ataxia type 31, hereditary dentatorubropallidoluysian atrophy, ataxia telangiectasia, Friedreich's ataxia, ataxia with vitamin E deficiency, aprataxin deficiency, senataxin deficiency, spastic ataxia of Charlevoix-Saguenay, hereditary spastic paraplegia, multiple system atrophy (olivopontocerebellar atrophy, Shy-Drager syndrome, striatonigral degeneration) and cortical cerebellar atrophy. Preferred are hereditary olivopontocerebellar atrophy, hereditary cortical cerebellar atrophy, spinocerebellar ataxia type 3 (Machado-Joseph disease), spinocerebellar ataxia type 6, spinocerebellar ataxia type 31 and cortical cerebellar atrophy.

Volumetric MRI (vMRI) enables in vivo assessment of brain structure volume, offering scales of the rate of atrophy.

Compound A or a salt thereof used in the present invention may be prepared by a method known per se or by combining such methods, or by the method disclosed in Patent Literature 1.

Compound A or a salt thereof used in the present invention may be blended with various pharmaceutical additives such as an excipient, a binding agent, a disintegrating agent, a disintegration inhibitor, a consolidation/adhesion-preventing agent, a lubricant, an absorption/adsorption carrier, a solvent, a bulking agent, an isotonic agent, a solubilizer, an emulsifier, a suspending agent, a thickener, a coating agent, an absorption enhancer, a gelling/procoagulant agent, a light stabilizer, a preservative, a desiccant, an emulsification/suspension/dispersion stabilizer, a color protecting agent, a deoxidant/antioxidant, a flavoring agent, a coloring agent, a foaming agent, an antifoaming agent, a soothing agent, an antistatic agent, a buffer, and/or a pH adjuster to give a pharmaceutical preparation such as an oral preparation (e.g., tablets, capsules, powders, granules, fine granules, pills, suspensions, emulsions, liquids, and syrups), injections, eye drops, nasal sprays and transdermal agents. Tablets are preferred as an oral dosage form for patients with AD.

The above agents are formulated by a usual method.

The method of administration of Compound A, which is not particularly limited, is accordingly determined based on the form of the preparation, the age, sex and other conditions of the patient and the level of symptoms of the patient.

The dose of Compound A is accordingly selected based on the administration, the age, sex, type of disease and other conditions of the patient.

The agent may be administered to an adult in a dose or divided doses of usually 40 to 500 mg in terms of Compound A per day. The agent is administered in a dose or divided doses of preferably 100 to 400 mg in terms of Compound A per day, and administered in a dose of further preferably 160 mg or 320 mg in terms of Compound A per day.

In the administration of Compound A or a salt thereof in the present invention, prevention or treatment by administration of acetylcholinesterase inhibitors (AChEIs) may also be included. Examples of AchEIs include donepezil hydrochloride, galantamine hydrochloride, rivastigmine tartrate and tacrine hydrochloride.

In the present invention, the subject may have undergone prevention or treatment by administration of AChEI for at least 6 months before administration of Compound A or a salt thereof.

Next, the present invention will be described with reference to Test Examples and Preparation Examples, but the present invention is not limited thereto.

Maleate of Compound A was used as the test compound.

Test Example 1 Multicenter Randomized Double-Blind Phase II Placebo-Controlled Trial for Assessing Effectiveness and Safety of Compound A in Mild to Moderate AD Patients Subject (selection criteria): Patients were screened in a period from 42 days before treatment assignment to the assignment based on the following selection criteria.
  Patients who were probable AD and are 55 years old or older and 85 years old or younger at the time of obtaining consent of screening.
  Patients with an MMSE score of 12 to 22 at the time of screening
  Patients with a Modified Hachinski Ischemia Scale score of 4 or less
  Patients who have been treated with a donepezil hydrochloride or rivastigmine transdermal system for at least 4 months before the baseline and with a stable dose thereof for 3 months before the baseline.
  In the case of patients who have received memantine in addition to being treated with a donepezil hydrochloride or rivastigmine transdermal system, patients who have been treated with memantine for at least 4 months before the baseline and with a stable dose thereof for 3 months before the baseline.
  Patients whose brain MRI or CT results match AD at the time of screening Organization of groups: Patients matched (484 patients) were randomly divided into the following 3 groups and the trial was started.
(1) High dose group: 224 mg of a test compound (160 mg in terms of Compound A) was orally administered once a day for 4 weeks and then 448 mg of a test compound (320 mg in terms of Compound A) was orally administered once a day for 48 weeks (158 patients)
(2) Low dose group: 224 mg of a test compound (160 mg in terms of Compound A) was orally administered once a day for 52 weeks (166 patients)
(3) Placebo group: placebo was orally administered once a day for 52 weeks (158 patients)

Method of Assessment:
Volumetric MRI
  Brain volume of subjects was measured by vMRI scan at the screening and after 52 weeks, and the volume change of the whole brain and the hippocampus of the subjects were quantified to assess brain atrophy based on the change from the screening.
  Furthermore, volume change of the whole brain and 101 areas (obtained by dividing the areas existing in both the left brain and the right brain of the Brodmann areas (1 to 52) into 101 areas) in each subject was quantified to assess brain atrophy based on the change from the screening.

Statistical Analysis:
  Changes in the volume of the whole brain and the hippocampus after 52 weeks from the baseline were compared between the high dose group and the placebo group, and between the low dose group and the placebo group based on Mixed-effect Models. For models, the treatment groups were included as a fixed effect, age, baseline of the respective brain volumes (the whole brain or the hippocampus), baseline of MMSE and ApoE4 genotype (positive/negative) were included as covariates, and trial sites were included as a random effect.
  Furthermore, changes in the respective volumes of the whole brain and the 101 areas after 52 weeks from the baseline were compared between the high dose group and the placebo group, and between the low dose group and the placebo group.

Results: shown below
  Change in brain volume obtained by vMRI scan at week 52 from the baseline is shown in Table 1, FIG. 1 and FIG. 2.

TABLE 1

| | | Brain volume | |
|---|---|---|---|
| Group | Number of cases/statistics | Whole brain (mL) | Hippocampus (mL) |
| High dose group | Number of cases | 76 | 76 |
| | Least square means (standard error) | −20.05(3.821) | −0.31(0.057) |
| | Difference from placebo group (95% Confidence interval) | 3.94(−2.91, 10.79) | 0.08(−0.02, 0.18) |
| | p-value | 0.2581 | 0.0996 |
| Low dose group | Number of cases | 79 | 79 |
| | Least square means (standard error) | −21.37(3.582) | −0.27(0.053) |
| | Difference from | 2.63(−4.15, 9.40) | 0.12(0.03, 0.22) |

TABLE 1-continued

| Group | Number of cases/statistics | Brain volume | |
|---|---|---|---|
| | | Whole brain (mL) | Hippocampus (mL) |
| | placebo group (95% Confidence interval) | | |
| | p-value | 0.4456 | 0.0106 |
| Placebo group | Number of cases | 89 | 89 |
| | Least square means standard error) | −23.99(3.599) | −0.39(0.054) |

For the change in the volume of the whole brain and the hippocampus at week 52 from the baseline, volume reduction tended to be smaller in the Compound A group than in the placebo group. The difference in effects on the change in hippocampal volume between the Compound A low dose group and the placebo group was statistically significant.

For change in brain volume obtained by vMRI scan at week 52 from the baseline, results for areas in which a statistically significant difference (p-value<0.05) was found in the comparison between the test compound low dose group and the placebo group are shown in Table 2.

TABLE 2

| No. | Placebo group | | Low dose group | | p-value | Brain area |
|---|---|---|---|---|---|---|
| | Mean value | Variance | Mean value | Variance | | |
| 1 | −2.0490 | 1.0716 | −0.9201 | 1.5655 | 0.0001 | Left-Cerebellum-White-Matter |
| 2 | −0.6899 | 0.7012 | −0.2695 | 0.6474 | 0.0005 | Left-Cerebellum-Cortex |
| 3 | −2.9861 | 1.4550 | −2.1332 | 1.4933 | 0.0013 | ctx-rh-superior temporal |
| 4 | −1.6919 | 1.3679 | −0.89 | 1.4082 | 0.0014 | Right-Cerebellum-White-Matter) |
| 5 | −2.6470 | 1.4373 | −1.9609 | 1.1486 | 0.0030 | ctx-lh-insula |
| 6 | −1.5952 | 0.5635 | −1.3142 | 0.5647 | 0.0054 | Whole_brain |
| 7 | −2.6510 | 1.4746 | −1.9976 | 1.1656 | 0.0056 | ctx-rh-insula |
| 8 | −0.7248 | 0.8780 | −0.3209 | 0.8541 | 0.0090 | Right-Cerebellum-Cortex |
| 9 | −3.2601 | 1.4409 | −2.6157 | 1.4466 | 0.0124 | ctx-rh-inferior temporal) |
| 10 | −1.5322 | 1.4680 | −0.8995 | 1.4382 | 0.0146 | ctx-rh-lateral orbitofrontal |
| 11 | −1.4416 | 0.8598 | −1.0753 | 0.8417 | 0.0157 | Right-Cerebral-White-Matte) |
| 12 | −3.8173 | 2.1618 | −2.97 | 1.9228 | 0.0195 | ctx-lh-entorhinal |
| 13 | −1.5679 | 0.8570 | −1.2418 | 0.7405 | 0.0215 | Left-Cerebral-White-Matter |
| 14 | −3.0880 | 1.7450 | −2.3402 | 1.9331 | 0.0232 | Left-Hippocampus |
| 15 | −0.5499 | 1.5192 | 0.1244 | 1.9565 | 0.0323 | ctx-lh-parsorbitalis |

In the Compound A low dose group, volume reduction of the cerebellum out of the whole brain and the 101 areas particularly tended to be suppressed compared to the placebo group (Nos. 1, 2, 4 and 8 in Table 2).

The same tendency as in the low dose group was observed in the Compound A high dose group.

Preparation Example 1

0.9726 g of magnesium stearate (magnesium stearate, Merck) was added to 174.03 g of maleate of Compound A and the mixture was mixed for 30 minutes. The mixed powder was compression-molded by a roller compactor (TF-LABO (roll pressure 3 MPa), Freund Corporation), and the solid obtained by molding was granulated. 49.51 g of lactose (FlowLac 90, Meggle Japan), 16.50 g of crystalline cellulose (CEOLUS PH302, Asahi Kasei Chemicals) and 6.67 g of croscarmellose sodium (Primellose, DMV Japan) were each sieved through a sieve with an opening of 850 μm and added to 60.0 g of the resulting granulated powder, and the mixture was mixed for 10 minutes. 0.6667 g of magnesium stearate was added to the mixed powder and the mixture was mixed for 30 minutes. The mixed powder was tableted by a tableting machine (HT-P18A, Hata Tekkosho) at a tableting pressure of about 12 kN using a pestle having a double rounded surface with a tablet diameter of 8.5 mm to obtain round uncoated tablets each weighing 250 mg. The uncoated tablets were coated with 8 mg of a coating agent per tablet using a film coater DRC-200 (Powrex), and then a small amount of carnauba wax (Polishing Wax-105, Nippon Wax) was added thereto to give film-coated tablets.

Preparation Example 2

60.90 g of mannitol (Parteck M200, Merck) and 3.60 g croscarmellose sodium were added to 53.70 g of maleate of Compound A and the mixture was mixed for 10 minutes. 1.80 g of magnesium stearate was added to the mixed powder and the mixture was mixed for 30 minutes. The mixed powder was tableted at a tableting pressure of about 10 kN using a pestle having a double rounded surface with a tablet diameter of 8.5 mm to obtain round uncoated tablets each weighing 250 mg. The uncoated tablets were coated with 8 mg of a coating agent (Opadry 03F44057, 00F440000 (hypromellose 2910: 71.5%, Macrogol 6000: 14.166%, talc: 7.167%, titanium oxide: 7.067%, iron sesquioxide: 0.1%), Colorcon Japan LLC) per tablet, and then a small amount of carnauba wax was added thereto to give film-coated tablets.

Preparation Example 3

11.11 g of magnesium stearate was added to 1988.89 g of maleate of Compound A and the mixture was mixed for 30 minutes. The mixed powder was compression-molded by a roller compactor, and the solid obtained by molding was granulated. To 107.13 g of the resulting granulated powder were added 26.21 g of mannitol, 7.50 g of ethyl cellulose (ETHOCEL 100FP Premium, The Dow Chemical Company), 3.75 g of crystalline cellulose (CEOLUS KG-1000, Asahi Kasei Chemicals), 3.75 g of crospovidone (Kollidon CL-SF, BASF) and 0.75 g of croscarmellose sodium, and the mixture was mixed for 30 minutes. 0.90 g of magnesium stearate was added to the mixed powder and the mixture was mixed for 5 minutes. The mixed powder was tableted at a tableting pressure of about 7 kN using a pestle having a double rounded surface with a tablet diameter of 8.5 mm to obtain round uncoated tablets each weighing 315 mg. The uncoated tablets were coated with 9 mg of a coating agent per tablet, and then a small amount of carnauba wax was added thereto to give film-coated tablets.

The invention claimed is:

1. A method of treating spinocerebellar ataxia, comprising administering 1-(3-(2-(1-benzothiophen-5-yl)ethoxy)propyl)azetidin-3-ol or a salt thereof to a patient.

2. The method of treating spinocerebellar ataxia according to claim 1, wherein the spinocerebellar ataxia is hereditary olivopontocerebellar atrophy, hereditary cortical cerebellar atrophy, spinocerebellar ataxia type 3 (Machado-Joseph disease), spinocerebellar ataxia type 6, spinocerebellar ataxia type 31 or cortical cerebellar atrophy.

3. The method of treating spinocerebellar ataxia according to claim 1, wherein the 1-(3-(2-(1-benzothiophen-5-yl)ethoxy)propyl)azetidin-3-ol or a salt thereof suppresses cerebellar atrophy in a patient with spinocerebellar ataxia.

4. The method of according to claim 1, wherein the 1-(3-(2-(1-benzothiophen-5-yl)ethoxy)propyl)azetidin-3-ol or a salt thereof improves ataxia in a patient with spinocerebellar ataxia.

5. The method of treating spinocerebellar ataxia according to claim 1, wherein the method improves balance disorder in a patient with spinocerebellar ataxia.

6. The method of treating spinocerebellar ataxia according to claim 1, wherein 1-(3-(2-(1-benzothiophen-5-yl)ethoxy)propyl)azetidin-3-ol or a salt thereof is orally administered in a dose of 100 mg to 400 mg once a day.

7. The method of treating spinocerebellar ataxia according to claim 1, wherein 1-(3-(2-(1-benzothiophen-5-yl)ethoxy)propyl)azetidin-3-ol or a salt thereof is orally administered in a dose of 160 mg or 320 mg once a day.

* * * * *